US005252830A

United States Patent [19]
Weinberg

[11] Patent Number: 5,252,830
[45] Date of Patent: Oct. 12, 1993

[54] DEDICATED APPARATUS AND METHOD FOR EMISSION MAMMOGRAPHY

[75] Inventor: Irving Weinberg, 9754 Whiskey Run, Laurel, Md. 20723

[73] Assignees: Irving Weinberg, Laurel, Md.; Frederick M. Mako, Fairfax Station, Va.; Ansel M. Schwartz, Pittsburgh, Pa.

[21] Appl. No.: 824,804

[22] Filed: Jan. 22, 1992

[51] Int. Cl.$^5$ .............................................. G01T 1/161
[52] U.S. Cl. ................................ 250/363.02; 378/37
[58] Field of Search ..................... 250/363.02, 363.04; 378/37

[56] References Cited

FOREIGN PATENT DOCUMENTS

| 0412734 | 2/1991 | European Pat. Off. | 250/363.04 |
| 0107183 | 8/1981 | Japan | 250/363.04 |
| 0092974 | 6/1983 | Japan | 250/363.04 |
| 0180477 | 10/1984 | Japan | 250/363.04 |
| 9100048 | 1/1991 | PCT Int'l Appl. | 250/363.04 |

*Primary Examiner*—Paul M. Dzierzynski
*Assistant Examiner*—Richard Hanig
*Attorney, Agent, or Firm*—Ansel M. Schwartz

[57] ABSTRACT

The present invention is an apparatus for examining a body part. The apparatus comprises a device for providing an anatomical image of the body part, such as an x-ray and a device for providing a physiological image of the body part in an adjacent relationship with said means for providing an anatomic image such that the body part remains in the same position during and between anatomic and physiological imaging. Preferably, the body part is infiltrated with a radiotracer and the device for providing a physiological image includes a device for detecting emissions of the radiotracers from the body part. In an alternative embodiment, the apparatus for examining a body part has a device for immobilizing the body part and a device for providing a physiological image of the body part. The providing device is in an adjacent relationship with the immobilizing means. Preferably, the apparatus includes a device for providing an anatomical image of the body part and the device for producing a physiological image includes means for detecting emissions of a radiotracer from the body part. The present invention is also a method for examining a body part of a patient which has the first step of obtaining an anatomical image of the body part. Then, there is the step of obtaining a physiological image of the body part such that the body part remains in the same position during and between anatomical and physiological imaging.

24 Claims, 1 Drawing Sheet

DEDICATED APPARATUS AND METHOD FOR EMISSION MAMMOGRAPHY

FIELD OF THE INVENTION

The present invention is related to a apparatus for medical examination. More specifically, the present invention is related to an apparatus and method for examining a body part infiltrated with a radiotracer.

BACKGROUND OF THE INVENTION

Mammography is currently the most effective method of screening for breast cancer. The goal of breast cancer screening is the detection of early non-palpable tumors. Although mammography is very sensitive in the detection of cancer, it is not very specific in determining whether mammographic abnormalities are due to benign or malignant disease (Limitations of Mammography in the Identification of Noninfiltrating Carcinoma of the Breast, S.F. Sener, F.C. Candela, M.L. Paige, J.R. Bernstein, D.P. Winchester, *Surgery Gynecology, and Obstetrics*, Aug. 1988, 167:135-140). Therefore, a noninvasive method of confirming the malignancy of suspicious mammographic abnormalities would be a major benefit in patient care. In this way, the number of benign excisional biopsies (approximately 75% of all excisional biopsies) can be reduced (R. Brem, personal communication).

When abnormal mammograms are encountered, the physician's options are limited. For minimally suspicious lesions, short-term repeat examination (four to six month follow-up) is often recommended. This may result in psychological stress for the patient and introduces the possibility of loss in patient follow-up due to scheduling or communication errors. The unlikely possibility of interim tumor growth cannot be definitely ruled out (Breast Cancer: Age-Specific Growth Rates and Screening Strategies, M. Moskowitz, *Radiology*, Oct. 1986, 161:37-41), especially in patients under fifty.

The role of ultrasound in clarifying the status of a mammographic abnormality is limited to the differentiation of solid masses from benign cysts. If the strict criteria for the ultrasonic appearance of a simple cyst are satisfied, the referring physician may be reassured that the lesion is benign. Unfortunately, the current spatial resolution of ultrasound makes the technique of limited value for lesions significantly smaller than five millimeters (R. Brem, personal communication).

Doppler ultrasound has been advocated as a means for differentiating benign from malignant masses, but results of clinical trials have been contradictory, and the doppler method has no current clinical role in breast imaging (The Role of US in Breast Imaging, V.P. Jackson, *Radiology*, Nov. 1990, 177:305-311).

Fine-Needle Aspiration (FNA) of breast masses is a technique whose sensitivity and specificity is operator dependent (Fine-Needle Aspiration Biopsies of Breast Masses, L. Palombini et. al., *Cancer*, Jun. 1, 1988, 61:2273-2277), and has been considered experimental (Discriminating Analysis Uncovers Breast Lesions, D.B. Kopans, *Diagnostic Imaging*, Sept. 1991, pp. 94-101). Because of its relatively low cost and reduced morbidity associated with surgery and anesthesia, FNA has been suggested as a possible replacement for excisional biopsy. Unfortunately, there is a high (13-50%) rate of insufficient samples when FNA is performed on non-palpable mammographically detected lesions. All of these cases of negative FNAs require excisional biopsy (Fine-Needle Aspiration Cytology in Lieu of Open Biopsy in Management of Primary Breast Cancer, H.J. Wanebo et al., *Annals of Surgery*, May 1984, 199 (5) pp. 569-579). Further, FNA as a non-imaging diagnostic modality, has the disadvantage that no information is obtained about the physical distribution of the detected tumor. As a cytopathological technique, FNA cannot easily differentiate between cases of marked dysplasia, carcinoma-in-situ, or invasive cancer. Fine-Needle Aspiration is generally not performed for non-palpable breast lesions.

Another option for the referral of a patient with equivocal mammographic anomalies is excisional biopsy of the breast in the area corresponding to the region of mammographic abnormality. The probability of malignancy ranges from 2% for a circumscribed solid mass to almost 90% for a spiculated ill-defined mass (Discriminating Analysis Uncovers Breast Lesions, D.B. Kopans, *Diagnostic Imaging*, Sep. 1991, pp. 94-101; R. Brem, personal communication). The true-positive fraction for biopsies obtained as a result of a mammographic screening program is between twenty and thirty percent (Nonpalpable Breast Lesions: Accuracy of Prebiopsy Mammographic Diagnosis, G. Hermann, C. Janus, I.S. Schwartz, B. Krivisky, S. Bier, J.G. Rabinowitz, *Radiology*. Nov. 1987 165:323-326; R. Brem, personal communication). Excisional biopsy has the additional disadvantage of introducing scarring, which may render interpretation of follow-up mammograms more difficult (Discriminating Analysis Uncovers Breast Lesions, D.B. Kopans, *Diagnostic Imaging*, Sep. 1991, pp. 94-101). An additional disadvantage to excisional biopsies is that, as a non-imaging modality, the physical distribution of the tumor is poorly described.

It is also known to use radionuclide imaging to detect cancers. 2-[F-18]-Fluoro-2-deoxy-D-glucose (FDG) is a radioactive analogue of glucose that is taken up preferentially by cancer cells (Primary and Metastatic Breast Carcinoma: Initial Clinical Evaluation with PET with the Radiolabeled Glucose Analogue 2-[F-18]-Fluoro-2-deoxy-D-glucose, R.L. Wahl, R.L. Cody, G.D. Hutchins, E.E. Mudgett, *Radiology* (1991) 179:765-770). A Fluorine-18 nucleus decays by emitting a positron which is annihilated within a few millimeters by an electron. The result of this annihilation is the production of two gamma rays that are approximately 180 degrees apart in direction (Positron Emission Tomography and Autoradiography, Edited by M.E. Phelps, J.C. Mazziotta, H.R. Schelbert, pp. 240-285, Raven Press, N.Y. 1986). After a patient has received an intravenous dose of FDG she may be examined with detectors that sense these gamma rays.

Previous detection methods have included imaging with a specially collimated planar gamma camera ([18-F] Fluorodeoxyglucose scintigraphy in diagnosis and follow up of treatment in advanced breast cancer, *European Journal of Nuclear Medicine* (1989) 15:61-66) and with a whole-body Positron Emission Tomography (PET) scanner (Primary and Metastatic Breast Carcinoma: Initial Clinical Evaluation with PET with the Radiolabeled Glucose Analogue 2-[F-18]-Fluoro-2-deoxy-D-glucose, R.L. Wahl, R.L. Cody, G.D. Hutchins, E.E. Mudgett, *Radiology* (1991) 179:765-770). PET imaging of breast cancer patients given FDG has been shown to be useful in imaging tumors as small as 3.2 cm and in patients whose breasts are too dense to be imaged well mammographically (Primary and Metastatic Breast Carcinoma: Initial Clinical Evaluation with PET with the Radiolabeled Glucose Analogue 2-[F-18]-Fluoro-2-deoxy-D-glucose, R.L. Wahl, R.L. Cody, G.D. Hutchins, E.E. Mudgett, *Radiology* (1991) 179:765–770).

The use of a specially collimated planar gamma camera to image the breast with this high resolution is limited by technical factors. The energy of 511 KeV is not well suited for acquisition by conventional gamma cameras, and the collimation required to correct for the high energy leads to loss of signal (counts/pixel) that is equivalent to resolution loss due to low photon flux.

Conventional PET imaging devices are designed to image the entire body. Accordingly, there are several disadvantages to employing a whole body PET scanner in a primary role as a high resolution confirmatory modality for small suspicious breast lesions. The first disadvantage of using a whole body PET scanner for breast imaging is the limited resolution available. The net resolution of a whole-body PET system is a combination of individual factors and is at best 5 mm FWHM (Michael Phelps, Ph.D., personal communication). The effect of this resolution limit is that radioactivity is underestimated (Positron Emission Tomography and Autoradiography, Edited by M.E. Phelps, J.C. Mazziotta, H.R. Schelbert, pp. 240–285, Raven Press, N.Y. 1986; Design of a Mosaic BGO Detector System for Positron CT, H. Uchida, T. Yamashita, M. Iida, S. Muramatsu, *IEEE Transactions on Nuclear Science* February 1986, NS-33 (1), pp. 464–467). This reduces the sensitivity of PET scanners in estimating the malignancy of mammographically detected lesions smaller than twice the resoltuion limit, and also precludes the use of the PET scanner in delineating tumor margins with high accuracy.

A second disadvantage of a conventional PET scanner for imaging of subtle lesions in the breast is the high cost of the examination. In order to accommodate the entire body, a conventional PET scanner must employ tens of hundreds of expensive detector arrays along with a gantry and associated electronics.

A third disadvantage of a PET scanner is that the PET image format would not be easily compared to conventional mammograms. This is due to the fact that the breast is an organ which can be compressed to an essentially two-dimensional object. The variability in internal architecture of the breast results in few landmarks for positioning, and the location of an anomaly on the mammographic image of the compressed breast does not always correspond to the same location in the non-compressed breast.

In order to achieve the highest spatial resolution available in a tomographic system, motion of the patient due to breathing must be limited. Immobilizing of the breast by compression is the most straightforward approach to solving this problem, but implementation within a PET scanner detector ring is impossible. Additionally, the use of PET scanner to image an essentially two-dimensional object such as a compressed breast is not economically rational.

High resolution (20 cm diameter bore) PET scanners, originally developed for animal studies, may soon be available commercially. For a system with smaller aperture (i.e. 20 cm bore for a dedicated head scanner) the resolution in the axial plane is 3.5 mm (Development of a High Resolution PET, T. Yamashita et al., *IEEE Transactions on Nuclear Science*, April 1990, Vol. 37 (2) pp. 594–599). Such a system would satisfy the goal of high resolution. A disadvantage would be the considerable cost of such relatively expensive scanners, with approximately fifteen detector arrays, as dedicated units for breast imaging. Further, the problems of immobilization of the breast and of comparison to standard mammography would still be unaddressed.

SUMMARY OF THE INVENTION

The present invention is an apparatus for examining a body part. The apparatus comprises a device for providing an anatomical image of the body part, such as an x-ray and a device for providing a physiological image of the body part in an adjacent relationship with said means for providing an anatomic image such that the body part remains in the same position during and between anatomic and physiological imaging.

Preferably, the body part is infiltrated with a radiotracer and the device for providing a physiological image includes a device for detecting emissions of the radiotracers from the body part.

Preferably, the radiotracer produces gamma rays, and the detecting device includes two detector modules, each of which has at least one array of gamma ray sensitive material.

Preferably, each detector module has shielding for reducing the undesirable emissions and is attached to a swing arm for allowing them to swing into and out of an operational position.

In an alternative embodiment, the apparatus for examining a body part has a device for immobilizing the body part and a device for providing a physiological image of the body part. The providing device is in an adjacent relationship with the immobilizing means.

Preferably, the apparatus includes a device for providing an anatomical image of the body part and the device for producing a physiological image includes means for detecting emissions of a radiotracer from the body part.

Preferably, the immobilizing device includes a table and a compression arm.

The present invention is also a method for examining a body part of a patient. The method has the step of immobilizing the body part in a preferred position. Then, there is the step of obtaining a physiological image of the body part. Preferably, before the immobilizing step, there is the step of injecting the patient with a radiotracer and after the immobilizing step, there is the step of obtaining an anatomical image of the body part.

The present invention is also a method for examining a body part of a patient which has the first step of obtaining an anatomical image of the body part. Then, there is the step of obtaining a physiological image of the body part such that the body part remains in the same position during and between anatomical and physiological imaging. Preferably, before the obtaining step, there is the step of immobilizing the body part.

BRIEF DESCRIPTION OF THE DRAWINGS

The present invention provides for a reduction in the number of cancer-free patients required to undergo surgical biopsy because of equivocal mammographic findings.

In the accompanying drawings, the preferred embodiment of the invention and preferred methods of practicing the invention are illustrated in which.

DESCRIPTION OF THE PREFERRED EMBODIMENT

Figure 1:
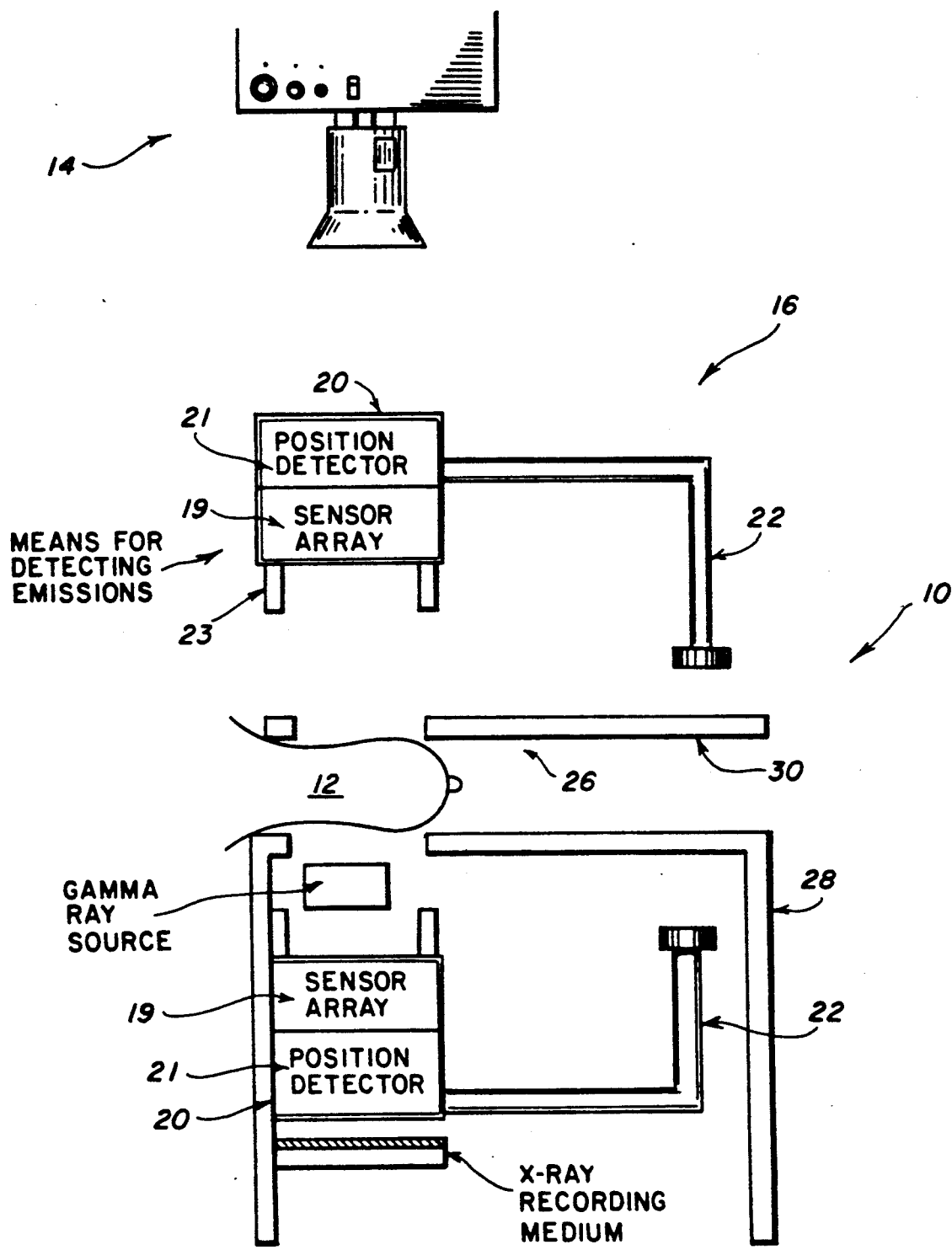
FIG. 1 is a schematic representation of the apparatus for examining a body part.

Referring now to the drawings wherein like reference numerals refer to similar or identical parts throughout the several views, and more specifically to FIG. 1 thereof, there is shown an apparatus 10 for examining a body part 12, such as a breast. The apparatus 10 includes means 14 for providing an anatomical image of the body part 12 and means 16 for providing a physiological image of the body part 12. The means 16 for providing a physiological image is disposed adjacent to the means 14 for providing an anatomical image such that the body part 12 remains in the same position during and between anatomical and physiological imaging. Preferably, the body part 12 is infiltrated with a radiotracer and the means 16 for providing a physiological image includes means for detecting emissions of the radiotracers from the body part 12. The radiotracers can be 2-[F-18]-fluoro-2-deoxy-D-glucose (FDG) or 16 alpha-[F-18]-fluoroestradiol-17 beta or other radiotracers. Preferably, the means for providing an anatomical image includes an x-ray source and x-ray recording medium, such as x-ray film. Alternatively, a digital radiography device can be used. Alternatively, other methods of anatomic imaging such as magnetic resonance can be used.

In a preferred embodiment, the radiotracer produces gamma rays and the detecting means includes two detector modules 20 each of which has at least one sensor array 19 of gamma ray sensitive material (scintillator), such as bismuth germanate crystals, mounted upon a position detector 21 such as a photomultiplier array. Alternatively, individual light sensors, such as position sensitive photomultipliers or avalanche photodiodes can be mounted upon each gamma ray detector in the array 19. In an alternative embodiment, each detector module 20 has a continous sheet of gamma ray material which is mounted upon a position sensitive multiplier or photomultiplier array. The continuous sheet of gamma ray sensitive material can have slots with septa on its surface which would operate in a manner similar to the block detectors known in the art of PET scanners.

Preferably, each detector module 20 has shielding 23 for reducing undesirable emissions. Preferably, each detector module 20 is attached to a swing arm 22 for allowing them to swing into and out of an operational portion. A gamma ray source can be used to yield a transmission image of the body part 12. Preferably, the apparatus 10 includes means 26 for immobilizing the body part 12, such as with compression. The immobilizing means 26 can include a table 28 and a compression arm 30 which compresses the body part 12 against the table 28.

In an alternative embodiment, the apparatus 10 is not limited to having means 14 for obtaining an anatomical image of the body part 12. The apparatus 10 includes means 26 for immobilizing the body part 12 and means 16 for providing a physiological image of the body part 12. The providing means 16 is in an adjacent relationship to the immobilizing means 26. Preferably, the immobilizing means 26 compresses the body part 12 and can include a table 28 upon which the body part 12 rests and a compression arm 30 which compresses the body part against the table 28.

The invention is also a method of examining a body part of a patient. The method includes the first step of immobilizing the body part in a preferred position. Then, there is the step of obtaining a physiological image of the body part. Preferably, before the immobilizing step, there is the step of injecting the patient with a radiotracer and the obtaining step includes the step of detecting emissions from the immobilized body part. The step of obtaining an anatomical image of the body part such as an x-ray can be performed before the immobilizing step. Preferably, before the immobilizing step, there is the step of performing a compression examination, such as a spot view compression examination.

The invention is also related to an alternative method of examining a body part of a patient. This method includes the first step of obtaining an anatomical image of the body part. Then, there is the step of obtaining a physiological image of the body part such that the body part remains in the same position during and between anatomical and physiological imaging. Preferably, before the obtaining step, there is the step of immobilizing the body part, such as with compression.

In the operation of the apparatus, a patient who is being examined for breast cancer would be injected with 2-[F-18]-Fluoro-2-deoxy-D-glucose (FDG). FDG is a radiotracer which is a radioactive analogue of glucose that is taken up preferentially by breast cancer cells. A more detailed explanation of this process is given in Primary and Metastatic Breast Carcinoma: Initial Clinical Evaluation with PET with the Radiolabeled Glucose Analogue 2-[F-18]-Fluoro-2-deoxy-D-glucose, R.L. Wahl, R.L. Cody, G.D. Hutchins, E.E. Mudgett, *Radiology* (1991) 179:765:770. FDG's nucleus decays by emitting a positron which is annihilated within a few millimeters by an electron. The result of this annihilation is the production of two gamma rays that are approximately 180° apart in direction.

Approximately one hour after injection with FDG, the patient undergoes a spot view breast compression examination. The breast 12 would then be immobilized and a magnification mammogram would be obtained for any areas suspicious for malignancy. If an abnormality is spotted on the mammographic film, high resolution detector modules 20 are swung in place above and below the compressed breast. Each detector module 20 consists of an array of bismuth germanate crystals which detect the gamma rays produced by the FDG. Each array is mounted upon a position photomultiplier. Electronic collimation using coincidence gating would yield high sensitivity to emitted radiation. The shielding reduces the number of undesirable emissions detected by the detector modules. Once the detector modules swing into place an image of the emissions is taken in areas of suspicion.

The rationale for the apparatus is the adaptation of the standard radiological mammographic geometry for gamma ray and single photon emitting radiotracers. The apparatus would incorporate (or be easily mounted upon) a conventional x-ray mammography unit for straightforward comparison with conventional mammograms.

The increased sensitivity allowed by the mammographic geometry is expected to permit imaging of suspicious areas in the breast within a short period of time (10-15 minutes), allowing the patient to remain in breast compression for the duration of the scan. Use of the invention would result in exact registration between the conventional mammogram and the image of radiotracer uptake. Advantages of the invention over existing technology include high resolution, low cost, and decreased morbidity.

The proximity of the detector modules to the breast in the proposed mammographic geometry will lead to resolution superior even to high resolution PET scanners.

The dose of radioactivity given to the patient will be similar to the dose presently used for whole body PET imaging of FDG (approximately five milliCuries), which is within the acceptable radiation dose for diagnostic nuclear medicine techniques. The morbidity associated with this dose must be compared to the morbidity associated with unnecessary excisional biopsy. For treatment planning, the morbidity may be compared to that associated with unnecessary mastectomy. For delineation of tumor margin, the morbidity should be compared to the local recurrence of tumor in an under-resected breast.

Positron emitters such as Fluorine-18 (half-life 110 minutes) can be purchased by breast imaging centers from cyclotrons in most major U.S. cities. Note that the use of the proposed dedicated breast imaging device does not preclude the possibility of following the examination with a whole body PET scanner (if available) when clinically indicated, i.e., to search for metastases in a patient with proven cancer. Additionally, the apparatus could be used in conjunction with more generally available radioisotopes that emit single photons.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for examining a body part comprising:
   means for immobilizing and compressing the body part;
   means for providing an internal anatomical image of the body part; and
   means for providing a physiological image of the body part in an adjacent relationship with said means for providing an internal anatomic image such that the body part remains in the same position during and between anatomic and radiotracer physiological imaging.

2. An apparatus as described in claim 1 wherein the body part is infiltrated with a radiotracer and the means for providing a physiological image includes means for detecting emissions of the radiotracers from the body part.

3. An apparatus as described in claim 2 wherein the radiotracer produces gamma rays, and the detecting device includes two detector modules, each of which has at least one array of gamma ray sensitive material in communication with a position detector.

4. An apparatus as described in claim 1 wherein the body part is infiltrated with a radiotracer that emits photons and the detecting means includes a photon detector module.

5. An apparatus as described in claim 3 wherein the means for providing an anatomical image includes an x-ray source and x-ray recording medium.

6. An apparatus as described in claim 4 wherein each detector module has shielding for reducing the undesirable emissions.

7. An apparatus as described in claim 6 wherein each detector module has a collimator.

8. An apparatus as described in claim 7 wherein each detector module is attached to a swing arm for allowing them to swing into and out of an operational position.

9. An apparatus as described in claim 8 including a gamma ray source to yield a transmission image of the body part.

10. An apparatus as described in claim 1 wherein the immobilizing means includes a table and a compression arm.

11. An apparatus for examining a body part comprising:
    means for immobilizing and compressing the body part; and
    means for providing a radiotracer physiological image of the body part, said providing means in an adjacent relationship with said immobilizing and compressing means.

12. An apparatus as described in claim 11 including means for providing an anatomical image of the breast.

13. An apparatus as described in claim 12 wherein the means for producing a physiological image includes means for detecting emissions of a radiotracer from the breast.

14. An apparatus as described in claim 13 wherein the means for providing an anatomical image includes an x-ray source and x-ray recording medium.

15. An apparatus as described in claim 14 wherein the immobilizing means includes a table and a compression arm.

16. A method for examining a body part of a patient comprising the steps of:
    immobilizing the body part in a preferred position such that the body part is compressed; and
    obtaining a radiotracer physiological image of the body part.

17. A method as described in claim 16 wherein before the immobilizing step, there is the step of injecting the patient with a radiotracer.

18. A method as described in claim 16 wherein after the immobilizing step, there is the step of obtaining an anatomical image of the breast.

19. A method as described in claim 18 wherein the step of obtaining an anatomical image of the breast includes the step of taking an x-ray of the body part.

20. A method as described in claim 16 wherein before the immobilizing step, there is the step of performing compression examination.

21. A method for examining a body part of a patient comprising the steps of:
    immobilizing the body part in a preferred position such that the body part is compressed:
    obtaining an internal anatomical image of the body part; and
    obtaining a physiological image of the body part such that the body part remains in the same position during and between anatomical and radiotracer physiological imaging.

22. A method as described in claim 20 wherein before the immobilizing step, there is the step of injecting the patient with a radiotracer and the step of obtaining a physiological image includes the step of detecting emissions of the radiotracer from the body part.

23. A method as described in claim 22 wherein before the immobilizing step, there is the step of performing compression examination.

24. A method as described in claim 21 wherein before the step of obtaining an anatomical image, there is the step of performing a spot view breast compression examination.

* * * * *